(12) United States Patent
Bedard et al.

(10) Patent No.: US 7,582,257 B2
(45) Date of Patent: Sep. 1, 2009

(54) OZONE STERILIZATION METHOD

(75) Inventors: Claudia Bedard, Sainte-Foy (CA); Sylvie Dufresne, Sainte-Foy (CA); Helene Leblond, Sillery (CA); Cynthia Martel, Saint-Foy (CA); Karine Martel, Sainte-Augustin-de-Desmaures (CA)

(73) Assignee: TSO3, Inc., Sainte-Foy, Quebec (CA)

( * ) Notice: Subject to any disclaimer, the term of this patent is extended or adjusted under 35 U.S.C. 154(b) by 0 days.

(21) Appl. No.: 10/553,736

(22) PCT Filed: Sep. 7, 2004

(86) PCT No.: PCT/CA2004/001637
§ 371 (c)(1), (2), (4) Date: Sep. 21, 2006

(87) PCT Pub. No.: WO2005/030275
PCT Pub. Date: Apr. 7, 2005

(65) Prior Publication Data
US 2007/0065335 A1 Mar. 22, 2007

(30) Foreign Application Priority Data
Sep. 26, 2003 (CA) .................... 2443046

(51) Int. Cl.
*A61L 2/20* (2006.01)
(52) U.S. Cl. .......................................... 422/27; 422/33
(58) Field of Classification Search ................... None
See application file for complete search history.

(56) References Cited

U.S. PATENT DOCUMENTS

| 4,764,351 A | * | 8/1988 | Hennebert et al. | ........... 422/292 |
| 5,069,880 A | | 12/1991 | Karlson | |
| 5,266,275 A | | 11/1993 | Faddis | |
| 5,334,335 A | | 8/1994 | Norville | |
| 5,527,508 A | * | 6/1996 | Childers et al. | ............... 422/33 |
| 2002/0085950 A1 | | 7/2002 | Robitaille et al. | |

FOREIGN PATENT DOCUMENTS

CA 2149133 5/1994

* cited by examiner

*Primary Examiner*—Elizabeth L McKane
(74) *Attorney, Agent, or Firm*—Diederiks & Whitelaw, PLC

(57) ABSTRACT

The invention relates to an improvement in a method for sterilizing an article in a sterilizing chamber by exposing the article to humidified ozone in at least two consecutive sterilizing cycles, the improvement comprising, after the first of said consecutive sterilizing cycles and before the second of said consecutive sterilizing cycles, removing from the sterilizing chamber any condensed water present.

15 Claims, 3 Drawing Sheets

OZONE STERILIZATION METHOD

FIELD OF THE INVENTION

The invention relates to methods of sterilization, in particular, methods of sterilization using humidified ozone.

BACKGROUND OF THE INVENTION

Sterilization is the destruction of any virus, bacteria, fungus or other micro-organism, whether in a vegetative or in a dormant spore state. Conventional sterilization processes for medical instruments have involved high temperatures (such as steam and dry heat units) or toxic chemicals (such as ethylene oxide gas, EtO). Steam sterilization with an autoclave has been the time-honoured method of sterilization. It is fast and cost effective. However, the autoclave destroys heat-sensitive instruments. Thus, since more and more heat-sensitive instruments such as arthroscopes and endoscopes are used in medical treatment, other types of sterilization are needed, especially cold sterilization.

Ethylene oxide may be used to cold sterilize heat-sensitive instruments. However, it has now been deemed by national health and safety organizations to be carcinogenic and neurotoxic. It also poses flammability problems and is thus usually used in combination with chlorofluorocarbons (CFC's) which themselves are now undesirable. Further, sterilization with ethylene oxide takes 14 to 36 hours.

A more efficient, safer, and less expensive sterilization agent is ozone ($O_3$). Ozone, especially humidified ozone, is a sterilizing gas. Ozone can easily be generated from oxygen, especially hospital grade oxygen. Oxygen is readily available in the hospital environment, usually from a wall or ceiling oxygen source, or, if mobility is required, from a portable "J" cylinder of oxygen.

Ozone is widely used in industry as an oxidising agent to bleach paper pulp, treat drinking water, and sterilize sewage water and food products. The amounts (concentrations) of ozone required in the sterilization gas for water purification are low, generally less than 40 mg/l (milligram per liter). However, higher concentrations, combined with critical humidity levels, are required to make ozone an effective sterilant of micro-organisms. Those high concentrations of ozone gas have to be combined with critical levels of humidity. The sterilization efficiency of ozone increases rapidly with increased relative humidity. A high relative humidity is required for ozone to penetrate the protective shells of micro-organisms. The presence of water vapour will also accelerate ozone reactions with organic substances. Sufficient relative humidity further helps the penetration of sterilization packaging by ozone.

Sterilization with ozone is more efficient and quicker than with EtO and requires few changes in user habits. Moreover, ozone-based processes are compatible for use with current packaging, such as sterile pouches and rigid containers.

Ozone sterilization requires substantially no aeration or cooling down of sterilized instruments, which can be used immediately following sterilization. This allows hospitals to reduce the cost of maintaining expensive medical device inventories. Ozone sterilization offers several other advantages. It produces no toxic waste, does not require the handling of dangerous gas cylinders, and poses no threat to the environment or the user's health. Stainless-steel instruments and heat-sensitive instruments can be treated simultaneously, which for some users will obviate the need for two separate sterilizers.

U.S. Pat. No. 3,719,017 discloses the use of a mixture of ozone gas with a very fine water mist in a sealed plastic bag container which contains an article to be sterilized. The method involves repeated evacuation and refilling of the plastic bag with a mixture of ozone gas and a very fine water mist. The air in the bag is exhausted and replaced with a pressurised mixture of ozone and water mist. Upon encountering the much lower pressure within the bag, the water particles from the pressurised mixture explode, forming a water mist. However, this system cannot generate a sufficiently high water vapour concentration to provide the high relative humidity required for thorough sterilization (at least 85% relative humidity).

U.S. Pat. No. 5,069,880 describes a device capable of generating a relative humidity of 85%. In the apparatus the ozone is bubbled through a water bath to increase the water content of the gas. Although ozone at 85% humidity can kill most micro-organisms, it does not meet the "worst case scenario" stipulated in North American standards. Moreover, the device is unable to generate humidity levels higher than 85%. In addition, injecting ozone while humidifying the chamber increases the contact time of the ozone with the instruments to be sterilized, which may result in oxidation damage to the instruments.

A minimum relative humidity level of 90% (95%±5%) is required to meet North American standards set by agencies such as the Food and Drug Administration and Health Canada.

Water evaporates at 100° C. at atmospheric pressure (1013 mbar or 760 Torr). Thus, various prior patents (see Faddis et al., U.S. Pat. Nos. 5,266,275; 5,334,355; and 5,334,622) teach sterilization systems wherein water is heated to above the boiling point to evaporate the water for injection into the ozone-containing gas produced by an ozone generator. The steam is heated to 120° C. Thus, the vapour upon injection into the ozone-containing gas will have a temperature close to 100° C. However, since the decomposition of ozone increases exponentially with temperature in the range of 20 to 300° C., injecting the water vapour at a temperature of about 120° C. leads to premature ozone decomposition. As a result, the effective ozone concentration in the gas produced by the ozone generator is reduced, thereby requiring significantly increased treatment times and the generation of larger amounts of ozone gas for each sterilization cycle. Thus, a more efficient and effective sterilization apparatus is desired for the sterilization of ozone at a relative humidity of above at least 90%.

U.S. patent application Ser. No. 10/005,786 (filed on Nov. 8, 2001 which is a continuation-in-part application of U.S. patent application Ser. No. 09/310,695 which was filed on May 12, 1999 and is now abandoned), which is hereby incorporated by reference, addresses these problems by applying a vacuum pressure to lower the boiling point of water below the temperature inside the sterilization chamber. Thus the teachings of this application provide an effective sterilization process.

As taught in this application, it is preferred to repeat the sterilization cycle at least once to give greater assurance of effective sterilization. Thus, after loading the sterilization chamber with the articles to be sterilized (such as medical instruments), a sterilization cycle includes exposing the articles to the humidified ozone sterilant and then removing the sterilant. Repeating this cycle thus includes exposing the articles again to humidified ozone sterilant and removing the sterilant.

Although this repeated sterilization method has proven very effective, technical problems have been encountered at times which reduce the efficiency of the method. It is critical that the right combination of ozone concentration and relative humidity is achieved in the sterilization process. Thus, these and other parameters which directly affect them are monitored. If values are detected which may compromise effective sterilization, the whole process is normally aborted and the procedure restarted from the beginning. Further, it has been observed that when this type of repeated sterilization cycle is used, sometimes certain components of articles to be sterilized, for example metal components such as hinges and locks with tight spaces and crevices are not adequately sterilized.

The present invention seeks to reduce the number of times the sterilization process is aborted and to increase the probability of effective sterilization.

SUMMARY OF THE INVENTION

It has now been found that a modification of the abovementioned repeated sterilization cycle, by inserting at least one additional step into the process, reduces the number of times the procedure must be aborted, and also improves the effective sterilization of medical instruments subjected to the process.

The improvement of the present invention is characterized by the additional step of removing any condensed water within the sterilization chamber after a sterilization cycle and, before starting a subsequent sterilization cycle.

According to one aspect of the present invention there is provided in a method for sterilizing an article in a sterilizing chamber by exposing the article to humidified ozone in at least two consecutive sterilizing cycles, the improvement comprising, after the first of said consecutive sterilizing cycles and before the second of said consecutive sterilizing cycles, removing from the sterilizig chamber any condensed water present.

According to another aspect of the present invention there is provided in a method for the sterilization of an article comprising at least two consecutive sterilization cycles, wherein the first of said consecutive cycles comprises the steps of: (a) providing a sterilization chamber; (b) placing the article into the sterilization chamber; (c) sealing the sterilization chamber; (d) maintaining the sterilization chamber operating temperature at about 20-35° C.; (e) applying a vacuum of a preselected vacuum pressure to the sterilization chamber, the vacuum pressure being adjusted to a level sufficient to lower the boiling point of water to a temperature at least as low as the temperature in the sterilization chamber; (f) humidifying the sterilization chamber by exposing an amount of water to the vacuum pressure in the sterilization chamber for evaporating the water, the amount of water being selected so that the water vapour produced is sufficient to achieve a relative humidity of 90-100% in the sterilization chamber; (g) supplying ozone-containing gas to the sterilization chamber; (h) maintaining the sterilization chamber sealed for a preselected treatment period; and (i) releasing the vacuum in the sterilization chamber and the second of said at least two consecutive sterilization cycles comprising repeating at least steps (e) to (h) the improvement comprising effecting an additional step between said first and second cycle wherein the additional step comprises (j) removing any condensed water from the sterilization chamber.

Without wishing to be bound by theory, it is believed that because of the high relative humidity used, after the step of applying the humidified ozone to the chamber and its contents, some condensation may occur on the chamber floor or walls. Condensation may also occur on articles in the sterilization chamber, for example, on metal parts and components of such articles. At the start of a repeat sterilization cycle, in a initial vacuum step, such condensed water would evaporate, lowering the temperature of the sterilization chamber of articles within the chamber and thus effectively creating "cold spots". In turn, any lowering of the temperature of the chamber or its contents, thus the presence of any such "cold spots", would increase the probability of further condensation of water vapour in the next humidification step which would thus reduce the water content of the chamber and thus reduce the relative humidity so that it may fall below the target level (preferably 95%) and the sterilization procedure would have to be aborted. Further, it is presently believed that the inadequate sterilization of ceratin components of articles to be sterilized, for example metal components such as hinges and locks, was due to condensation which formed a barrier to the ozone and thus prevented adequate sterilization. By introducing at least one additional step to remove condensation, it is now believed that such components are made more accessible to the sterilizing humidified ozone in a subsequent sterilization cycle.

The removal of condensed water may be referred to as a post-exposure step since it follows at least a first sterilization cycle and thus an exposure to the humidified ozone sterilant. However, it may be more appropriately referred to as a conditioning or re-conditioning step (since in preferred processes it may not be the first conditioning step and is intended to return the conditions within the chamber to conditions at least approximating those at the start of the sterilization).

Removal of condensed water in the re-conditioning step is preferably accomplished by flushing the sterilization chamber with an inert gas, or a gas which can serve as a vehicle for the removal of moisture in the form of water vapour, but which will not interfere with sterilization.

The preferred gas is oxygen. Although nitrogen gas is applicable, it is preferred to avoid the use of nitrogen, or nitrogen containing mixtures, such as air, since under the conditions of the sterilization process which uses ozone, a powerful oxidising agent, some nitric acid may be formed which may corrode or damage components of the medical instruments. For similar reasons, other gases, such as sulfur-containing gases, which form corrosive oxidation products, should also be avoided. Oxygen itself does not form any such corrosive compounds under the sterilization process conditions and is thus an available gas for the post-exposure step. Further, as mentioned above, oxygen sources are readily available in hospital environments where the process of the invention is likely to be most useful.

Throughout this description, units of pressure will be variously indicated in mbar, Torr, atmospheres or ¼ Torr. 1 atmosphere equals 760 Torr or 1013 mbar.

One or more ventilating cycles can be added to the preferred method for removing the remaining ozone and humidity from the sterilization chamber.

BRIEF DESCRIPTION OF THE DRAWINGS

The invention will be described in more detail in the following by way of example only and with reference to the attached drawings wherein.

DETAILED DESCRIPTION OF THE PREFERRED EMBODIMENT

Figure 1:
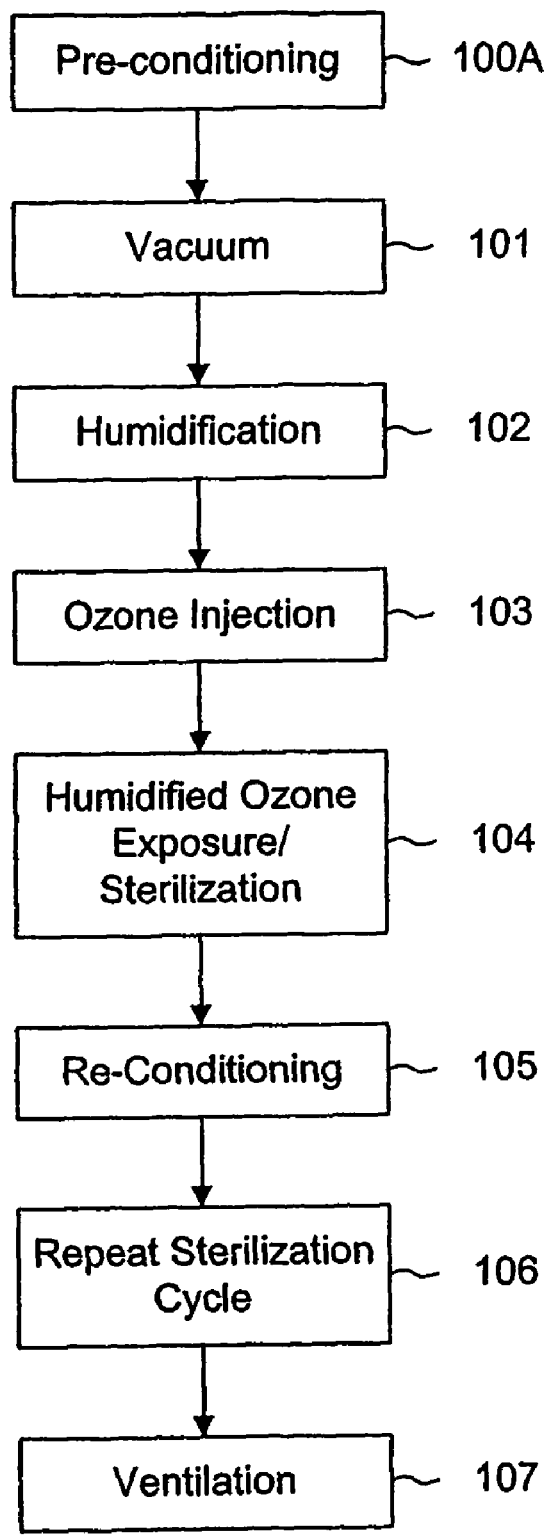
FIG. 1 is a flow diagram of a method in accordance with the invention.
Figure 2:
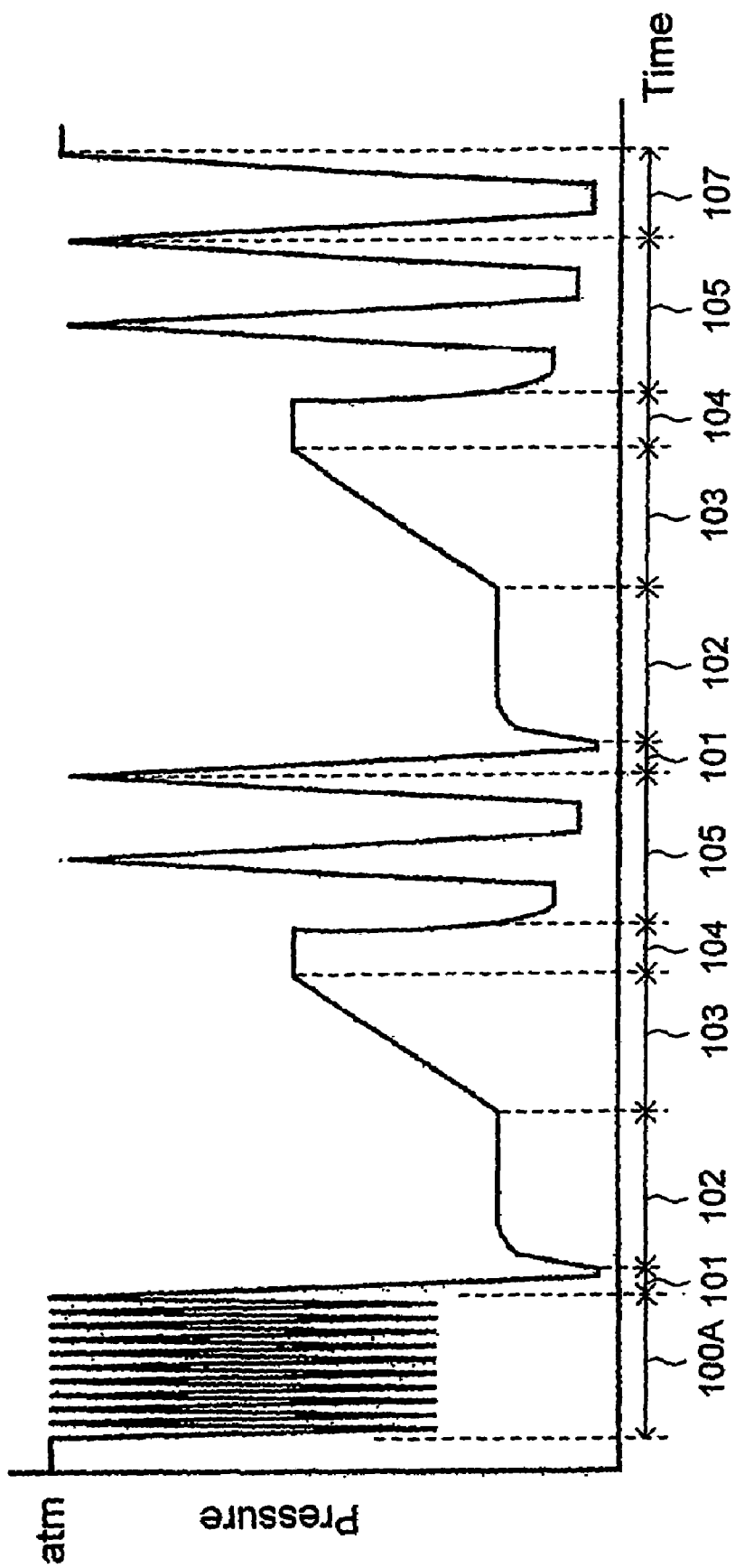
FIG. 2 is a graph to illustrate the sequence of steps in a method in accordance with the invention by plotting pressure against time.

As can be seen from FIGS. 1 and 2, the process can be regarded as including six or seven basic steps, some of which may be repeated in a second sterilization cycle.

FIG. 1 is a schematic representation of a sterilization process according to the invention, showing the steps of the process in sequence. FIG. 2 is another representation of a process according to the invention. FIG. 2 illustrates the process by showing the various steps as a function of the pressure. Thus the vertical axis shows the pressure, with atmospheric pressure represented at the top end of the vertical axis and zero pressure (or complete vacuum) at the bottom end of the vertical axis. The horizontal axis represents the sequence of steps in the process from left to right and thus corresponds to elapsed time, although not necessarily to any scale, but only for the purpose of illustration.

Since the present invention is mainly concerned with the humidification step, it will be understood that details of other process steps are in the nature of preferred features which are not essential to the broadest aspects of the invention.

As mentioned above, the essential steps in a sterilization cycle comprise exposing instruments to be sterilized to a sterilant and removing the sterilant. When the sterilant is humidified ozone, care must be taken to ensure not only that sufficient ozone is used to effect sterilization, but that sufficient humidity exists during sterilization to maximize the effect of sterilization. The following discussion represents preferred procedures and modifications which have been found to be suitable for such a humidified ozone sterilization process.

As shown in FIGS. 1 and 2, preferably the sterilization is preceded by a conditioning step, indicated as step 100A. This step may also be referred to as a pre-conditioning step. In this step, after inserting the articles to be sterilized in a sterilization chamber, the chamber is sealed Generally, it is preferred to effect the sterilization at a target temperature in the range of from about 25 to 40° C., more preferably from about 30 to 36° C. and especially at around 30° C., for example at 30.8° C. The walls of the chamber are preferably maintained at around this sterilization temperature. Since this is above usual room temperature, it is preferred to successively fill and empty the chamber, with ambient air, in a succession of pulses. This pulsing helps stabilize the conditions in the chamber and helps bring any load (instruments to be sterilized) to the preferred chamber temperature. This is represented by the peaks and troughs shown in FIG. 2 in the left-hand portion of the graph indicated as 100A, which represents the pre-conditioning step. The peaks represent a pressure of around atmospheric pressure and thus represent at least partially filling the chamber with ambient air. The troughs represent reduced pressure or evacuations of the chamber. Room temperature is usually around 18 to 22° C. so to reach a target temperature of, for example, 30° C., the air must be heated. The walls of the sterilization chamber are preferably heated. Thus by pulsing a quantity of air into and out of the chamber, the temperature of the air and the temperature of the load (any instruments in the chamber for sterilization), approaches the target chamber temperature of around 30° C. Generally it is preferred that a reduced pressure in the range of from about 350 to about 450 Torr, more preferably about 250 Torr, is used to evacuate the chamber in each of the evacuation pulses in this pre-conditioning step. It is preferred that the ambient air load is pulsed from 7 to 16 times, more preferably ten times. However, the number of such pulses may be increased or decreased to bring the load of ambient air to a satisfactory temperature.

Any inert gas may be used as the gas in the pre-conditioning step. The choice of gas will be governed by costs or by consideration of whether it will interfere with the sterilant in the subsequent sterilization steps. In later steps, it is preferred to avoid using air since the nitrogen which it contains may form harmful substances, such as nitrogen oxides as a result of the powerful oxidizing capacity of ozone. Such nitrogen oxides may then form traces of nitric acids with any water vapour and may thus damage parts, such as metal parts, of articles to be sterilized. However, in this pre-conditioning step, air can be used, although oxygen would be preferred.

The next step is a vacuum step and is indicated as 101 in FIGS. 1 and 2. In this step, gaseous contents of the sterilization chamber are evacuated. It is preferred to use a deep vacuum, generally in the range of from about 5 to 0.5 Torr, more preferably about 2.5 to 0.5 Torr, more particularly, less than 1.25 Torr to remove as much of the gaseous contents as possible. It is preferred to apply this pressure for a time in the range of from about 30 seconds to 5 minutes, more preferably about a minute to allow the pressure to stabilize within the chamber, especially considering that the articles to be sterilized may well include containers and pouches.

The next step is a humidification step and is indicated as 102 in FIGS. 1 and 2. This step is to provide the sterilization chamber with the humidity required for sterilization. Water from a water reservoir is evaporated and introduced into the chamber as water vapour until the relative humidity is equal to or above the target value. It is preferred that the relative humidity during sterilization is at least above 90%, preferably 95% or higher. It is preferred that after the target humidity is reached, conditions are maintained to stabilize and equilibrate the conditions throughout the chamber and the articles in the chamber. Preferably conditions are maintained for a time in the range of from about 10 to 50 minutes, more preferably for at least 30 minutes.

The next step is an ozone injection step which is represented as step 103 in FIGS. 1 and 2. Ozone is generated by an ozone generator. It is preferred to monitor the ozone produced by the generator to ensure that a sufficient quantity of ozone will be introduced to the sterilization chamber. Thus preferably the ozone generator is activated before the end of the humidification step so that sufficient ozone is being generated by the time it is required at the end of the humidification step. For a sterilization chamber of about 125 Liters, an ozone generation of between 160 and 200 mg/L at normal temperature and pressure (NTP) from the generator is preferred. Preferably, used ozone and unrequired ozone is catalytically destroyed (by conversion to oxygen) before expelling it to the atmosphere to avoid pollution.

A suitable ozone generator produces ozone from oxygen (preferably extra-dry medical grade oxygen) which is submitted to an electrical field produced inside the generator, suitably at a high frequency voltage of about 10,000 volts peak to peak. The high voltage permits a corona discharge in the generator cells to convert the oxygen to ozone. Ozone is heat sensitive, so it is preferred to keep the ozone generator operation at around 2 to 4° C. to optimise ozone production. When ready, the ozone is introduced into the humidified chamber until the ozone in the chamber preferably reaches a concentration in the range of about 45 to 100 mg/L NTP, more preferably about 85 mg/L NTP. Coupled with the high humidity, this concentration is considered to be sufficient to achieve sterilization.

The next step is the humidified ozone exposure step which is indicated as step 104 in FIGS. 1 and 2. This step involves maintaining the level of ozone and humidity achieved from the previous steps for a time sufficient to achieve a satisfactory level of sterilization. A time period of from 5 minutes to 1 hour may be needed, although 15 minutes is preferred. This step completes the first sterilization cycle. In the interest of maximising the assurance of sterilization, it is preferred to repeat the sterilization with at least a second sterilization cycle, preferably including repeating at least steps 101, 102, 103 and 104.

However, as noted above, according to the present invention, it has been found that before starting a second or other additional sterilization cycle, there should be a reconditioning step. Thus the next step, according to the invention, is a re-conditioning step which is indicated as step 105 in FIGS. 1 and 2. The purpose of this step is to remove any condensed water. Preferably all, or substantially all of the condensed water is removed and preferably all, or substantially all of the water vapour is removed in this step. It is preferred that the amount of water removed is from about 75% to 100% by weight of all the water in the chamber, more preferably from about 80% to 100%. Thus this step may be regarded as a flushing or purging step to remove condensed water. It is also preferred that the temperature of the chamber is restabilized to the target temperature, for example, the preferred temperature of 30.8° C. The gaseous vehicle used for this purging or flushing step is preferably a gas which is inert in the context of the sterilization process. For example, as previously mentioned, nitrogen and other gases which may form undesirable oxygenated products by contact with ozone are preferably avoided. In this step, since it follows a previous sterilization cycle which has used ozone, it is preferred to avoid the use of air because of the high nitrogen content of air. The preferred gas for this step is oxygen, especially medical grade dry oxygen, which would usually be readily available in an environment in which the sterilization process of the invention would normally be used, such as a hospital. The reconditioning step preferably includes, or is preceded by, a vacuum step to remove humidity and ozone from the chamber. Preferably a vacuum in the range of about 20 down to 5 Torr, more preferably less than 10 Torr, is applied. Gaseous contents removed from the chamber are passed to a catalyst to convert any ozone to oxygen, for environmental reasons. It is preferred to maintain the low pressure such as the preferred pressure of 10 Torr for a period of time, preferably 2 to 3 minutes, to allow gaseous contents within articles in the chamber (especially articles having pouches and containers) to equilibrate with the rest of the chamber, to optimise removal. Medical grade oxygen is then introduced to the chamber. It is preferred that this re-conditioning step include at least one repetition of the vacuum and oxygen injection steps to optimise the removal of all condensation.

When all the sterilization cycles have been completed, a ventilation step is effected, which is indicated as 107 in FIGS. 1 and 2. The purpose of this step is to remove ozone and water vapour before the sterilization chamber is opened and the sterilized articles are removed.

It will be readily understood by a person skilled in the art that the sequence of some of the steps may be varied without compromising sterilization. Some steps might be effected simultaneously although the successive sequence described above is preferred.

Figure 3:
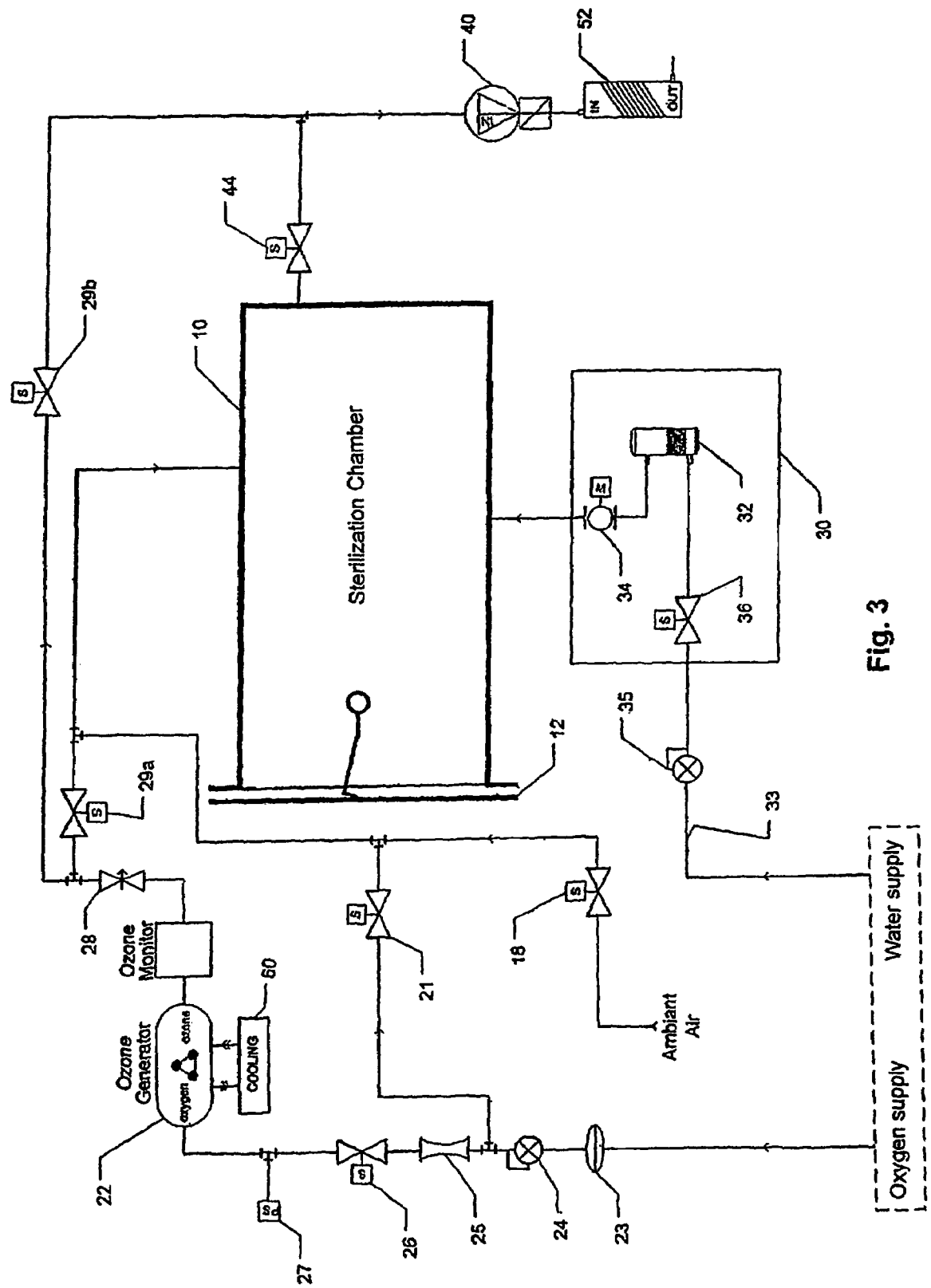
FIG. 3 is a schematic illustration of an apparatus suitable for use with the method of invention.

An ozone sterilizer apparatus, suitable for use with the method of the invention is illustrated schematically in FIG. 3. Medical quality oxygen is subjected in an ozone-generating unit including an ozone generator 22 to an electrical field, which partially converts the oxygen into ozone. The ozone is then fed into a humidified sterilization chamber 10 where it sterilises medical devices. The ozone is subsequently reconverted into oxygen using an ozone converting unit 52. The only residues left at the end of the sterilization cycle are oxygen and clean water vapour.

The apparatus includes a heated sterilization chamber 10 which can be sealed to contain a vacuum. This is achieved with an access door 12, which can be selectively opened for access into the chamber and which seals the chamber in the closed condition. The apparatus further includes ozone generator 22 for supplying ozone-containing gas to the sterilization chamber, a humidifier arrangement 30 for supplying water vapour to the sterilization chamber, and a vacuum pump 40 (a suitable pump is a dry scroll vacuum pump manufactured by Anestiwata). The vacuum pump 40 is used for the application of a sufficient vacuum to the sterilization chamber 10 to increase the penetration of the sterilizing gas and to be able to boil water at a temperature below the temperature inside the sterilization chamber. The vacuum pump 40 in the preferred embodiment is capable of producing a sufficient vacuum in the sterilization chamber to lower the boiling point of water in the chamber below the temperature in the chamber. In the preferred apparatus, the vacuum pump is capable of producing a vacuum of 0.1 mbar. Ozone produced in the ozone-generating unit 22 is destroyed in an ozone converting unit 52 to which ozone-containing gas is fed either after passage through the sterilization chamber 10 or directly from the ozone-generating unit 22 through valve 29b. The ozone piping circuit includes an ozone converting catalyst (such as DEST 25, manufacturer TSO3). The ozone converting unit 52 is connected in series before or after the vacuum pump 40 to prevent ozone gas escaping to ambient air. The ozone decomposing material in the preferred catalyst is carulite. For economic and practical reasons, it is preferred to use a catalyst to decompose the ozone exhausted from the sterilization chamber 10. The catalyst destroys ozone on contact and converts it into oxygen with a certain amount of heat being produced. Catalysts of this type and their manufacture are well known to the person skilled in the art of ozone generators and need not be described in detail herein. Furthermore, other means for destroying the ozone contained in the sterilization gas will be readily apparent to a person skilled in the art. For example, the gas can be heated for a preselected time to a temperature at which the ozone decomposition is accelerated, for example, to 300° C.

The humidifier arrangement 30 includes a humidifier chamber 32 (such as HUM 0.5, manufacturer TSO3) sealed from ambient air and connected to the sterilization chamber 10 through a conduit and a vapour intake valve 34. The humidifier chamber 32 is equipped with a level control to ensure a sufficiently high water level (not shown). Water is directly supplied to the humidifier chamber 32 from a drinking or purified water supply connection. Water is supplied to the humidifier chamber 32 by way of a filter 33, a pressure regulator 35, and input valve 36. The water vapour produced in the humidifier chamber 32 enters the sterilization chamber 10 by way of a vapour intake valve 34. The ozone-generating unit includes an ozone generator 22 (such as OZ, model 14a, manufacturer TSO3) of the corona discharge type, which is cooled to decrease the ozone decomposition rate, as is well known in the art. To achieve a good lethality rate in an ozone sterilization process, the ozone supplied in the sterilization chamber should be sufficient to obtain a concentration of 48 to 96 milligrams per liter, preferably 50 to 90 milligrams per liter. At these concentrations, the ozone generation is associated with a relatively high energy loss in the form of heat. Generally, about 95% of the supplied electrical energy is converted into heat and only 5% is used to produce ozone.

Since heat accelerates the inverse transformation of ozone into oxygen, it must be removed as quickly as possible by cooling the ozone generator 22. The ozone generator in the apparatus is kept at the relatively low temperature of 3 to 6° C. by either an indirect cooling system with cooling water recirculation, or a direct cooling system with a refrigeration unit for cooling. The cooling system 60 is preferably kept at the temperature of 3 to 6° C. In the preferred embodiment, the cooling system is kept at 4° C. so that the ozone-containing gas generated by unit 22 is at the ambient temperature of around 20 to 35° C., preferably 30° C. Thus, the ozone-containing gas entering into the sterilization chamber for humidification and sterilization is kept at ambient temperatures of from 20 to 35° C. This means that ozone decomposition is kept to a minimum and that the sterilization process is more efficient.

The ozone-generating unit is preferably supplied with medical quality or medical grade oxygen. The apparatus can be connected to a wall oxygen outlet common in hospitals or to an oxygen cylinder or to any other source capable of supplying the required quality and flow. The supply of oxygen to the generator 22 takes place across a filter 23, a pressure regulator 24, a flow metre 25 and an oxygen shut-off valve 26. The generator is protected against oxygen over-pressure by a safety pressure switch 27. The ozone-oxygen mixture generated by the generator 22 is directed to the sterilization chamber 10 by a needle valve 28 and a mixture supply solenoid valve 29a. The mixture can also be directly supplied to the ozone converting unit 52 by way of a bypass solenoid valve 29b. In a preferred embodiment which includes a sterilization chamber of 125 liters volume, the pressure regulator 24 preferably controls the oxygen input at a flow rate of about 1.5 liters per minute. However, it will be readily apparent to the skilled person that other flow rates may be used depending on the make and model of the ozone generator 22 and the size of the sterilization chamber.

The apparatus in accordance with the invention preferably includes a closed circuit cooling system using no fresh water.

The vacuum in the sterilization chamber 10 is produced by the vacuum pump 40 and across the ozone converting unit 52 and the sterilization chamber drainage valve 44.

Operation

As mentioned above, the preferred sterilization method includes the following general steps as illustrated by the flow chart of FIG. 1. The medical instruments to be sterilized are sealed in sterile packaging containers or pouches such as generally used in the hospital environment and then placed into the sterilization chamber. The door of the sterilization chamber is closed and locked and the preconditioning phase is started by applying a vacuum to the sterilization chamber. Water vapour is admitted into the sterilization chamber to humidify the chamber contents. A mixture of ozone and oxygen is supplied to the chamber and the chamber maintained sealed for a preselected treatment period. In accordance with the present invention, before repeating the sterilization cycle, a re-conditioning step is effected to remove any condensed water. Then the vacuum application and ozone supply steps are repeated at least once. To remove all remaining ozone in the sterilization chamber 10 when the sterilization cycle is completed a ventilation phase begins. After the ventilation phase is complete, the door is unlocked and the sterilized material is removed from the chamber.

Before the sterilization cycle begins, the humidifier chamber 32 is filled with water to an adequate level, which is sufficient to satisfy the requirements for the whole sterilization cycle. This is done by temporarily opening the water-input valve 36. Valve 36 remains closed for the whole remainder of the sterilization cycle. In the first phase of the sterilization cycle, intake valve 18, oxygen shut-off valve 26, mixture supply valve 29a, and mixture by pass valve 29b (optional) are closed and vapour intake valve 34, and chamber drainage valve 44, are opened. The sterilization chamber 10 is evacuated to a vacuum pressure of about 0.1 mbar. Water vapour inlet valve 34 closes when the absolute pressure in the sterilization chamber falls below 60 mbar. Once a pressure of about 1,0 mbar is achieved, the chamber drainage valve 44 closes and the vapour intake valve 34 opens to lower the pressure in the humidifier chamber 32 to the vacuum pressure in the sterilization chamber. That forces the water in the humidifier chamber to boil and evaporate and to enter the sterilization chamber 10 as water vapour. Shortly before the end of the humidification period (usually about 2 to 6 min. before the end of the humidification period), the ozone generator is activated. The flow of the oxygen/ozone mixture exiting the ozone generator is controlled by ozone mixture supply valve 29. The apparatus preferably further includes a regulator valve 28 capable of resisting the vacuum and of adjusting the flow to between 1 and 12 liters per minute. As an optional feature, the generator can be started at the same time as the humidification period begins. This is then achieved with shut-off valve 26 and mixture by pass valve 29b. Shut-off valve 26 opens to let oxygen enter the generator. The ozone-oxygen mixture produced by the generator is then guided directly into the ozone converting unit 52 through mixture bypass valve 29b and vacuum pump 40. After a humidification period of approximately 30 minutes, the oxygen-ozone mixture is guided into the sterilization chamber by opening the mixture supply valve 29a and closing the mixture bypass valve 29b. The oxygen-ozone mixture enters the chamber 10 until an ozone concentration of 85 milligrams per liter in the chamber is achieved. The time required for this step is dependent on the flow rate and concentration of the ozone gas in the mixture (preferably 10% to 12% by weight). At this point in time, the mixture supply valve 29a is closed to seal off the sterilization chamber and to maintain the humidified ozone/oxygen gas mixture in the chamber under vacuum.

Once the sterilization chamber is filled with the humidified sterilization gas (mixture of oxygen and ozone gas), the generator 22 is stopped, the oxygen shut-off valve 26 is closed, and the ozone is maintained in contact with the articles to be sterilized for about 15 minutes, for a sterilization chamber of a volume of 125 liters (4 cubic feet). At this stage, the sterilization chamber is still under the effect of a partial vacuum of about 670 mbar. In an optional second step, the pressure level is raised to about 900 mbar using oxygen as a filing gas. This pressure level is maintained for about 20 mm. After the sterilization period, the vacuum is reapplied, preferably at a pressure of about 1.0 mbar again. Once the vacuum reaches 0.1 mbar, the humidification phase is recommenced, followed by the renewed injection of an oxygen/ozone sterilization gas mixture, followed by the sterilization period. The cycle of applying a vacuum of about 1.0 mbar, injecting sterilization gas, humidifying and sterilizing, can be repeated, and the number of repeat sterilization cycles (mini cycles) selected to achieve complete sterilization of the instruments. Preferably, between any two successive sterilization cycles, a re-conditioning step is effected, as described above, to remove any condensed water from the sterilization chamber. The number of repeat cycles used in an experimental set-up of a method in accordance with the invention including a 125 liters (4 cubic foot) chamber was 2 repeat cycles. This set-up conformed to the Security Assurance Level standards of the FDA (SAL 10-6).

To remove all remaining ozone and humidity in the sterilization chamber 10 after complete sterilization (after all successive sterilization cycles) a ventilation phase is engaged. The ventilation phase begins after the last sterilization cycle. The chamber drainage valve 44 opens and the vacuum is applied down to approximately 13 mbar. Vapour intake valve 34 closes when the pressure reaches 60 mbar to evacuate the remaining ozone in the humidifier. Once the vacuum pressure of 13 mbar is obtained, drainage valve 44 closes and the intake valve 21 opens, admitting oxygen into the sterilization chamber 10. Once atmospheric pressure is reached, intake valve 21 is closed, the sterilization chamber drainage valve 44 opened, and vacuum reapplied until a pressure of 13 mbar is reached. The ventilation cycle is then repeated twice. Once the atmospheric pressure is reached after the last cycle, the door mechanism of the sterilization chamber is activated to permit access to the contents of the sterilization chamber. The ventilation phase has two functions. First, to remove all ozone residues in the sterilization chamber before opening the access door and, second, to ensure that the sterilized material is dry, which is achieved by evaporation of all possibly present condensation when the vacuum pressure is applied.

The ozone-containing gas evacuated from the sterilization chamber 10 is passed over the ozone decomposing catalyst 52 of the ozone converting unit 50 prior to exhausting the gas to the atmosphere to ensure a complete decomposition of the ozone in the sterilization gas. The ozone generator 22 is used during only two portions of the sterilization cycle, the activation of the generator 22 (with optional valves 29a and 29b) and the evacuation of the sterilization chamber 10. During the startup phase of the generator 22, the mixture bypass valve 29b is opened and the ozone is guided across the catalyst. Once the start-up phase of the generator 22 is complete, the bypass valve 29b closes. During evacuation of the sterilization chamber 10, the sterilization chamber drainage valve 44 is opened and the ozone containing sterilization waste gas guided to the catalyst. Once the evacuation of the sterilization chamber 10 is completed, the drainage valve 44 is closed. The circulation of ozone is ensured by the vacuum pump 40, which operates during the whole sterilization cycle including all repeat cycles. If the ozone decomposing catalyst is located upstream of the vacuum pump this also ensures that the carulite is kept as dry as possible in order to avoid fouling of the catalytic material. Since the vacuum pump 40 is running during the whole. sterilization process, the carulite is exposed to reduced pressures, even if it is not used for the decomposition of ozone. This forces evaporation of water contained in the catalyst, which may have been absorbed by the carulite during the evacuation of the sterilization chamber. If located downstream of the vacuum pump, the catalyst is preferably heated to keep the carulite sufficiently dry.

A system, such as the one described above, suitable for use with the method of the invention is capable of maintaining a relative humidity level of 90%, preferably 95%±5% or higher, throughout the sterilization cycle.

The energy needed to evaporate the water during the humidification phase is taken from many sources. It is taken from the structure of the humidifier unit and the sterilization chamber and from the material to be sterilized. This contributes to a further cooling of the chamber, and its contents. In effect, at 20° C., water boils up to an absolute pressure of 23.3 mbar and 35° C., water boils up to an absolute pressure of 56.3 mbar. The vacuum in the sterilization chamber is preferably adjusted to a pressure where the boiling temperature of water is lowered below the temperature in the sterilization chamber. That boiling temperature may be so low that, depending on the energy available from the surrounding structure and gases, the water in the humidifier chamber will freeze before it gets vaporized. The humidifier may also be cooled by the evaporation process to a point where condensation freezes to the external surface of the humidifier. This can be avoided by heating the external surface of the humidifier sufficiently to keep the exterior of the humidifier unit and the water inside the humidifier chamber at room temperature, preferably at or above the temperature of the sterilization chamber. This is achieved with a heating arrangement (not illustrated) which will be readily apparent to the person of skill in the art.

The water vapour generated in the humidifier unit increases the relative humidity in the sterilization chamber. The humidification phase is continued until the relative humidity of the gas surrounding the medical instruments contained in the packaging pouches and containers reaches a minimum of 95%±5%, preferably 100%. For a sterilization chamber of an approximate volume of 125 liters, the water vapour admission increases the pressure to about 53 mbar in the sterilization chamber.

Oxygen/ozone-containing sterilization gas is injected into the humidified sterilization chamber at ambient temperature. For optimum operation of a sterilizer having a 125 liters chamber, a system is preferably used which is capable of generating an ozone flow in the range of about 1 to about 6 liters per minute, more preferably about 1.5 to 2 liters per minute, containing from about 160 to 200 mg/l of ozone to obtain at least a total of around 10,000 mg of ozone for each of the fillings of the sterilization chamber.

Changes and modifications in the specifically described embodiments can be carried out without departing from the scope of the invention which is intended to be limited only by the scope of the appended claims.

The invention claimed is:

1. In a method for sterilizing an article in a sterilizing chamber by exposing the article to humidified ozone containing gas in at least a pair of first and second consecutive sterilizing cycles, the improvement comprising, after the first sterilizing cycle and prior to the second sterilizing cycle, removing from the sterilizing chamber any condensed water present by applying a vacuum to the chamber and, thereafter, effecting a step of flushing the chamber with a gas that does not form oxygenated products by contact with ozone.

2. A method according to claim 1, wherein the gas is oxygen.

3. A method according to claim 2, wherein the flushing step is repeated at least once.

4. A method according to claim 1, wherein the temperature in the chamber is stabilized before the start of the second sterilizing cycle.

5. In a method for the sterilization of an article comprising at least two consecutive sterilization cycles, wherein the first of said consecutive cycles comprises the steps of:
   (a) providing a sterilization chamber;
   (b) placing the article into the sterilization chamber;
   (c) sealing the sterilization chamber;
   (d) maintaining the sterilization chamber operating temperature at about 20-35° C.;
   (e) applying a vacuum of a preselected vacuum pressure to the sterilization chamber, the vacuum pressure being adjusted to a level sufficient to lower the boiling point of water to a temperature at least as low as the temperature in the sterilization chamber;
   (f) humidifying the sterilization chamber by exposing an amount of water to the vacuum pressure in the sterilization chamber for boiling the water, the amount of water being selected so that the water vapour produced is sufficient to achieve a relative humidity of 90-100% in the sterilization chamber;
(g) supplying ozone-containing gas to the sterilization chamber;
(h) maintaining the sterilization chamber sealed for a preselected treatment period; and
(i) releasing the vacuum in the sterilization chamber;
and the second of said at least two consecutive sterilization cycles comprising repeating at least steps (e) to (h) the improvement comprising:
effecting an additional step between said first and second cycle wherein the additional step comprises (j) removing any condensed water from the sterilization chamber by effecting a step of flushing the chamber with a gas that does not form oxygenated products by contact with ozone.

6. A method of claim 5, wherein the sterilization chamber is maintained at an operating temperature of about 30° C.

7. A method of claim 6, wherein the vacuum pressure is between 0.1 and 10 mbar.

8. A method of claim 7, wherein the vacuum pressure is between 0.5 and 2 mbar.

9. A method of claim 5, wherein the steps (e) to (g) are repeated a number of times sufficient to ensure complete sterilization of the article and wherein step (j) is repeated after each sterilization cycle except the last cycle.

10. A method according to claim 5, wherein the gas is oxygen.

11. A method according to claim 10, wherein the flushing step is repeated at least once.

12. A method according to claim 5, wherein the temperature of the chamber is stabilized before the start of said second sterilizing cycle.

13. A method according to claim 5 wherein the step of removing from the sterilizing chamber any condensed water present further comprises applying a vacuum to the sterilization chamber before flushing the chamber with the gas that does not form oxygenated products by contact with ozone.

14. In a method for sterilizing an article in a sterilizing chamber by exposing the article to humidified ozone containing gas in at least a pair of first and second consecutive sterilizing cycles, the improvement comprising, after the first sterilizing cycle and prior to the second sterilizing cycle, removing from the sterilizing chamber any condensed water present by, in the substantial absence of any sterilant, effecting a step of applying a vacuum to the sterilizing chamber and then flushing the chamber with a gas that does not form oxygenated products by contact with ozone.

15. A method according to claim 14, wherein the flushing step is repeated at least once.

* * * * *

UNITED STATES PATENT AND TRADEMARK OFFICE
CERTIFICATE OF CORRECTION

PATENT NO. : 7,582,257 B2  Page 1 of 1
APPLICATION NO. : 10/553736
DATED : September 1, 2009
INVENTOR(S) : Bedard et al.

It is certified that error appears in the above-identified patent and that said Letters Patent is hereby corrected as shown below:

On the Title Page Item (56) should read

(56)          References Cited

US PATENT DOCUMENTS

| | | |
|---|---|---|
| 4,517,159 | 05/1985 | Karlson |
| 4,764,351 * | 08/1988 | Hennebert et al. |
| 5,069,880 | 12/1991 | Karlson |
| 5,266,275 | 11/1993 | Faddis |
| 5,334,335 | 08/1994 | Norville |
| 5,527,508 * | 06/1996 | Childers et al. |
| 5,868,999 | 02/1999 | Karlson |
| 2002/0085950 | 07/2002 | Robitaille et al. |

Item (56) should read

FOREIGN PATENT DOCUMENTS

| | | |
|---|---|---|
| CA | 2149133 | 05/1994 |
| WO | 95/25714 | 10/1995 |
| WO | 03/039607 | 05/2003 |

* cited by examiner

Signed and Sealed this

Twenty-second Day of December, 2009

David J. Kappos
*Director of the United States Patent and Trademark Office*